United States Patent [19]

Henning et al.

[11] Patent Number: 5,225,414

[45] Date of Patent: Jul. 6, 1993

[54] SUBSTITUTED AZOLES, A PROCESS FOR THEIR PREPARATION, AND THEIR USE

[75] Inventors: Rainer Henning, Hattersheim am Main; Adalbert Wagner; Hermann Gerhards, both of Hofheim am Taunus; Bernward Schölkens, Kelkheim/Taunus, all of Fed. Rep. of Germany

[73] Assignee: Hoechst Aktiengesellschaft, Frankfurt am Main, Fed. Rep. of Germany

[21] Appl. No.: 731,989

[22] Filed: Jul. 18, 1991

[30] Foreign Application Priority Data

Jul. 21, 1990 [DE] Fed. Rep. of Germany ....... 4023215

[51] Int. Cl.⁵ .................. A61K 31/505; A61K 31/44; C07D 487/00; C07D 487/02
[52] U.S. Cl. .................................... 514/258; 514/300; 514/303; 546/118; 546/121; 544/263
[58] Field of Search ........ 546/114, 121, 118; 514/299, 301, 300, 303, 258; 544/263

[56] References Cited

U.S. PATENT DOCUMENTS

| | | | |
|---|---|---|---|
| 3,642,813 | 2/1972 | Kirchmayr | 548/255 |
| 4,273,782 | 1/1981 | Cross et al. | 514/397 |
| 4,908,364 | 3/1990 | Thorwart et al. | 514/243 |

FOREIGN PATENT DOCUMENTS

0399731 11/1990 European Pat. Off. .
0420237 4/1991 European Pat. Off. .

OTHER PUBLICATIONS

Duncia et al., Journal of Medicinal Chemistry, 33(5) 1312–1329 (1990).
Carini et al., Chemical Abstracts, 109(5) 129,008 (1988) Abstract of EP 253,310.

*Primary Examiner*—Mukund J. Shah
*Assistant Examiner*—Matthew V. Grumbling
*Attorney, Agent, or Firm*—Finnegan, Henderson, Farabow, Garrett & Dunner

[57] ABSTRACT

The invention relates to compounds of the formula (I)

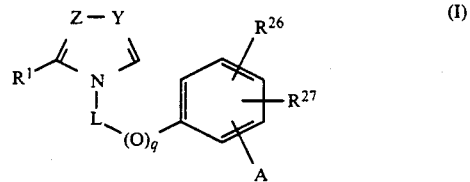

in which X, Y and Z are identical or different and are N or $CR^2$, and the other radicals have the meaning defined in the description, a process for the preparation thereof, agents containing these, and the use thereof.

4 Claims, No Drawings

SUBSTITUTED AZOLES, A PROCESS FOR THEIR PREPARATION, AND THEIR USE

DESCRIPTION

EP-A 324 377, EP-A 253 310, EP-A 288 833 and EP-A 323 841 disclose derivatives of imidazole, pyrrole, pyrazole and triazole, respectively, and the use thereof as antagonists of angiotensin II receptors.

Novel compounds of the azole type which are highly effective antagonists of angiotensin II receptors both in vitro and in vivo have now been found.

The invention relates to compounds of the formula (I)

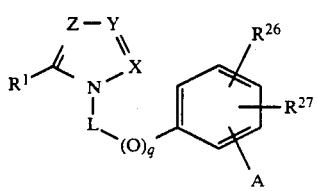

in which
a) X, Y and Z are identical or different and are N or $CR^2$,
b) $R^1$ is 1. $(C_2-C_{10})$-alkyl,
2. $(C_3-C_{10})$-alkenyl,
3. $(C_3-C_{10})$-alkynyl,
4. $OR^3$,
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $-(CH_2)_m-B-(CH_2)_n-R^4$,
10. benzyl,
11. a radical which is as defined under b) 1., 2., 3. or 9. and is monosubstituted with $CO_2R^3$,
12. a radical which is as defined under b) 1., 2., 3. or 9. and in which 1 to all hydrogen atoms are replaced by fluorine, or
13. the radical defined under b) 10. which is substituted on the phenyl with 1 or 2 identical or different radicals from the series comprising halogen, $(C_1-C_4)$-alkoxy and nitro;
c) $R^2$ is
1. hydrogen,
2. halogen,
3. nitro,
4. $C_vF_{2v+1}$,
5. pentafluorophenyl,
6. cyano,
7. phenyl,
8. phenyl-$(C_1-C_3)$-alkyl,
9. $(C_1-C_{10})$-alkyl,
10. $(C_3-C_{10})$-alkenyl,
11. phenyl-$(C_2-C_6)$-alkenyl,
12. -imidazolyl-$(CH_2)_m-$,
13. 1,2,3-triazolyl-$(CH_2)_n-$,
14. tetrazolyl-$(CH_2)_m-$,
15. $-(CH_2)_{0-1}-CHR^7-OR^5$,
16. $-(CH_2)_0-O-CO-R^3$,
17. $-(CH_2)_0-S-R^6$,
18. $-S(O)_x-R^6$,
19. $-CH=CH-(CH_2)_m-CHR^3-OR^6$,
20. $-CH_2=CH-(CH_2)_m-CO-R^8$,
21. $-CO-R^8$,
22. $-CH=CH-(CH_2)_m-O-CO-R^7$,
23. $-(CH_2)_m-CH(CH_3)-CO-R^8$,
24. $-(CH_2)_0-CO-R^8$, 25. 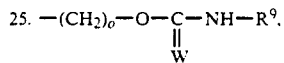

26. 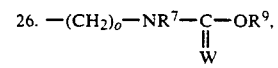

27. $-(CH_2)_o-NR^7-CO-NHR^9$,

28. $-(CH_2)_o-NR^7-SO_2R^9$,

29. 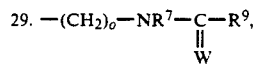

30. $-(CH_2)_nF$,

31. $-(CH_2)_n-O-NO_2$,

32. $-CH_2-N_3$,

33. $-(CH_2)_n-NO_2$,

34. $-CH=N-NR^5R^7$, 35. phthalimido-$(CH_2)_n-$,

36. 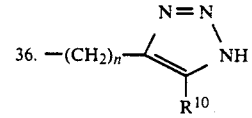

37. 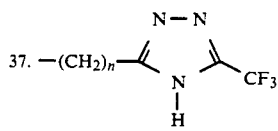

38. 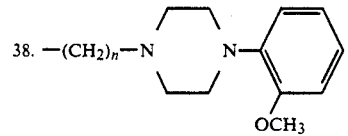

39. 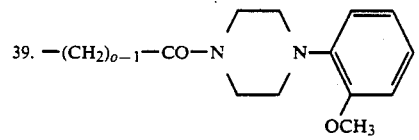

40. phenyl-$SO_2-NH-N=CH-$,

41. 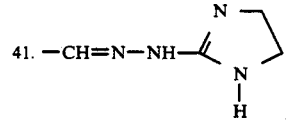

42. $-(CH_2)_n-SO_2-NR^7-CO-NR^6R^9$,
43. $-(CH_2)_o-SO_2R^9$,
44. a radical which is as defined under c) 7. or 8. and is substituted on the phenyl with 1 or 2 identical or different radicals from the series comprising halogen, hydroxyl, methoxy, trifluoromethyl, $CO_2R^3$ and phenyl,
45. a radical which is as defined under c) 9. or 10. or 18. and in which 1 hydrogen atom is replaced by hydroxyl or in which 1 to all hydrogen atoms are replaced by fluorine, or 46 the radical defined under c) 13. which is substituted with 1 or 2 identical or different radicals from the series comprising methoxycarbonyl and $(C_1-C_4)$-alkyl;

d) $R^3$ is
1. hydrogen,
2. $(C_1-C_8)$-alkyl
3. $(C_3-C_8)$-cycloalkyl,
4. phenyl,
5. benzyl or
6. the radical defined under d) 2. in which 1 to all hydrogen atoms are replaced by fluorine;

e) $R^4$ is
1. hydrogen,
2. $(C_1-C_6)$-alkyl,
3. $(C_3-C_8)$-cycloalkyl,
4. $(C_2-C_4)$-alkenyl or
5. $(C_2-C_4)$-alkynyl;

f) $R^5$ is
1. hydrogen,
2. $(C_1-C_6)$-alkyl,
3. $(C_3-C_8)$-cycloalkyl,
4. phenyl or
5. benzyl;

g) $R^6$ is
1. hydrogen,
2. $(C_1-C_6)$-alkyl,
3. $(C_3-C_8)$-cycloalkyl,
4. $(C_6-C_{12})$-aryl, preferably phenyl,
5. benzyl,
6. $(C_1-C_9)$-heteroaryl, which can be partially or completely hydrogenated, preferably 2-pyrimidinyl,
7. $(C_1-C_4)$-alkanoyl,
8. a radical which is as defined under g) 4. or 6. and is substituted with 1 or 2 identical or different radicals from the series comprising halogen, hydroxyl, methoxy, nitro, cyano, $CO_2R^3$ and trifluoromethyl, $NR^{11}R^{12}$ or

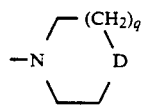

9. $(C_1-C_9)$-heteroaryl-$(C_1-C_3)$-alkyl, it being possible for the heteroaryl moiety to be partially or completely hydrogenated;

h) $R^7$ is
1. hydrogen,
2. $(C_1-C_6)$-alkyl,
3. $(C_3-C_8)$-cycloalkyl,
4. $(C_6-C_{12})$-aryl-$(C_1-C_6)$-alkyl, preferably benzyl,
5. phenyl or
6. $(C_1-C_9)$-heteroaryl;

i) $R^8$ is
1. hydrogen,
2. $(C_1-C_6)$-alkyl,
3. $(C_3-C_8)$-cycloalkyl,
4. phenyl-$(CH_2)_q$—,
5. $OR^5$,
6. $NR^{11}R^{12}$ or 7. 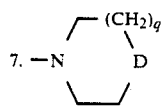

j) $R^9$ is
1. $(C_1-C_6)$-alkyl,
2. 1-adamantyl,
3. 1-naphthyl,
4. 1-naphthylethyl,
5. phenyl-$(CH_2)_q$— or
6. the radical defined under j) 1. in which 1 to all hydrogen atoms are replaced by fluorine;

k) $R^{10}$ is cyano, nitro or $CO_2R^7$;

l) $R^{11}$ and $R^{12}$ are identical or different and are
1. hydrogen,
2. $(C_1-C_4)$-alkyl,
3. phenyl,
4. benzyl or
5. α-methylbenzyl;

m) D is $NR^{13}$, O or $CH_2$;

n) $R^{13}$ is hydrogen, $(C_1-C_4)$-alkyl or phenyl;

o) A is the radical of a heterocycle which has 5–10 ring atoms and can be mono- or bicyclic and of which up to 9 ring atoms are carbon atoms, which can be substituted with up to 6, preferably up to 3 identical or different radicals $R^{14}$ or —$(CH_2)_{n-1}$—$(CHR^6$—$CH_2)_{0-1}$—$R^{15}$, and which can be unsaturated or partially hydrogenated;

p) $R^{14}$ is
1. halogen,
2. oxo,
3. nitroso,
4. nitro,
5. amino
6. cyano,
7. hydroxyl,
8. $(C_1-C_6)$-alkyl,
9. $(C_1-C_4)$-alkanoyl,
10. $(C_1-C_4)$-alkanoyloxy,
11. $CO_2R^3$,
12. methanesulfonylamino,
13. trifluoromethanesulfonylamino,
14. —CO—NH—$OR^9$,
15. —$SO_2$—$NR^6R^7$,
16. —$CH_2$—$OR^7$,
17. $(C_1-C_9)$-heteroaryl-$(CH_2)_q$—, preferably 1-tetrazolyl,
18. $(C_7-C_{13})$-aroyl, 19. 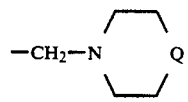

20. 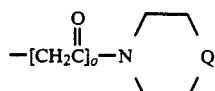

21. $(C_6-C_{12})$-aryl;

q) $R^{15}$ is
1. hydrogen,
2. $(C_1-C_6)$-alkyl,
3. $(C_3-C_8)$-cycloalkyl,
4. $(C_6-C_{12})$-aryl, 5. $(C_7-C_{13})$-aroyl,
6. $(C_1-C_4)$-alkoxy,
7. $(C_1-C_4)$-alkanoyloxy,
8. $(C_1-C_9)$-heteroaryl,
9. $CO_2R^3$,
10. halogen,
11. cyano,
12. nitro,
13. $NR^6R^7$,
14. hydroxyl,
15. $-CO-NH-CHR^5-CO_2R^3$,
16. sulfo,
17. $-SO_3R^3$,
18. $-SO_2-NR^7-CO-NR^6R^9$,
19. $-NR^7-CO-NR^6-SO_2-CH_2-R^5$,
20. $-C(CF_3)_2OH$,
21. phosphonooxy,
22. $-PO_3H_2$,
23. $-NH-PO(OH)_2$,
24. $-S(O)_rR^6$,
25. $-CO-R^8$,
26. $-CO-NR^6R^9$,
27. $-CR^{20}(OH)-PO(OH)_2$,
28. the radical defined under p) 20., 29. 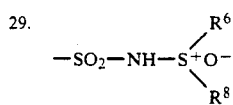

30. 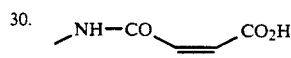

31. 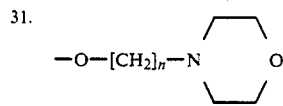

32. 5-tetrazolyl$-NH-CO-$,

33. $-CO-NH-NH-SO_2CF_3$,

34. 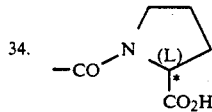

35. 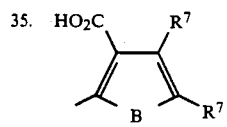

36. 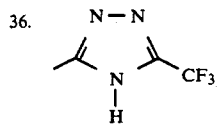

37. 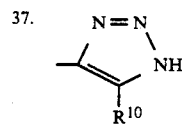

38. 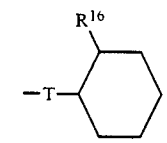

39. 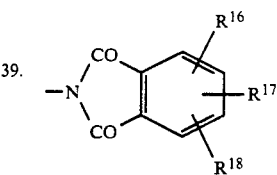

40. $-CO-NH-SO_2-R^{19}$ or
41. the radical defined under q) 4. which is substituted with 1 or 2 identical or different radicals from the series comprising halogen, cyano, nitro, $NR^6R^7$ and hydroxyl;

r) B is O, $NR^7$ or S;
s) W is O or S;
t) L is $(C_1-C_3)$-alkanediyl;
u) $R^{16}$ is $CO_2R^3$ or $CH_2CO_2R^3$;
v) $R^{17}$ is hydrogen, halogen, $(C_1-C_4)$-alkyl or $(C_1-C_4)$-alkoxy;
w) $R^{18}$ is hydrogen, $(C_1-C_4)$-alkyl or phenyl;
x) $R^{19}$ is
  1. $(C_1-C_4)$-alkyl
  2. $(C_3-C_8)$-cycloalkyl,
  3. phenyl,
  4. benzyl or
  5. the radical defined under x) 1. in which 1 to all hydrogen atoms are replaced by fluorine or chlorine;
y) T is
  1. a single bond,
  2. $-CO-$,
  3. $-CH_2-$,
  4. $-O-$,
  5. $-S-$,
  6. $NR^{21}-$,
  7. $-CO-NR^{21}-$,
  8. $-NR^{21}-CO-$,
  9. $-O-CH_2-$,
  10. $-CH_2-O-$,
  11. $-S-CH_2-$,
  12. $-CH_2-S-$,
  13. $-NH-CR^{20}R^{22}-$,
  14. $-NR^{21}-SO_2-$,
  15. $SO_2-NR^{21}-$,
  16. $-CR^{20}R^{22}-NH-$,
  17. $-CH=CH-$,
  18. $-CF=CF-$,
  19. $-CH=CF-$,
  20. $-CF=CH-$,
  21. $-CH_2-CH_2-$,
  22. $-CF_2-CF_2-$,
  23. $-CH(OR^3)-$,
  24. $-CH(OCOR^5)-$, 25. $-\overset{|}{\underset{NR^{23}}{C}}-$ or 26. 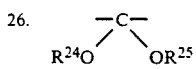

z) $R^{20}$ and $R^{22}$ are identical or different and are hydrogen, $(C_1-C_5)$-alkyl, phenyl, allyl or benzyl;

a') $R^{21}$ is hydrogen, $(C_1-C_6)$-alkyl, benzyl or allyl;

b') $R^{23}$ is
  1. $NR^{20}R^{21}$,
  2. ureido,
  3. thioureido,
  4 toluene-4-sulfonyl or
  5. benzenesulfonylamino;

c') $R^{24}$ and $R^{25}$ are identical or different and $(C_1-C_4)$-alkyl or together are $-(CH_2)_q-$;

d') $R^{26}$ and $R^{27}$ are identical or different and are
  1. hydrogen,
  2. halogen,
  3. nitro,
  4. $(C_1-C_4)$-alkyl or
  5. $(C_1-C_2)$-alkoxy;

e') Q is $CH_2$, NH, O or S;

f') m is an integer from 0 to 5;

g') n is an integer from 1 to 5;

h') o is an integer from 1 to 10;

i') q is 0 or 1;

j') r is 0, 1 or 2, or k') v is an integer from 1 to 6;

and the physiologically tolerated salts thereof.

Alkyl, alkenyl and alkynyl can be straight-chain or branched. A corresponding statement applies to radicals derived therefrom such as alkanoyl or alkoxy.

Cycloalkyl also mean alkyl-substituted rings.

$(C_6-C_{12})$-Aryl is, for example, phenyl, naphthyl or biphenylyl, preferably phenyl. A corresponding statement applies to radicals derived therefrom such as aroyl or aralkyl.

$(C_1-C_9)$-Heteroaryl means, in particular, radicals which are derived from phenyl or naphthyl in which one or more CH groups have been replaced by N and/or in which at least two adjacent CH groups have been replaced by S, NH or O (for the formation of a five-membered aromatic ring). Furthermore, 1 or both atoms at the condensation point of bicyclic radicals (as in indolizinyl) can also be a nitrogen atom.

Examples are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl quinolyl, isoquinolyl, phthalazinyl, quinoxalinyl, quinazolinyl, cinnolinyl.

Examples of the meaning of the heterocycle $AH_2$ from which the radical A is derived are furan, thiophene, pyrrole, imidazole, pyrazole, triazole, oxazole, isoxazole, thiazole, isothiazole, pyridine, pyridazine, pyrimidine, pyrazine, indole, indazole, quinoline, isoquinoline, phthalazine, quinoxaline, quinazoline, cinnoline, benzothiophene, benzofuran, coumarin, chroman, benzothiazole, benzoxazole, benzisothiazole, benzoxazine, benzothiazine, imidazolopyridine, imidazolopyrimidine, imidazolopyrazine, imidazolopyridazine, imidazolotriazine, imidazolothiazole, imidazoloisothiazole, pyrazolopyridine, thienopyridine, furopyridine, oxazolopyridine, oxazolopyrimidine and pyrrolopyrimidine. If the heterocycle is partially hydrogenated, preferably one radical remains aromatic.

A is linked from the isocyclic or from the heterocyclic moiety via an alkanediyl bridge L.

By physiologically tolerated salts of compounds of the formula I are meant both their organic and inorganic salts as are described in Remington's Pharmaceutical Sciences, 17th Edition, page 1418 (1985). For reasons of physical and chemical stability and solubility, preferred for acid groups are, inter alia, sodium, potassium, calcium and ammonium salts; for basic groups are, inter alia, salts with hydrochloric acid, sulfuric acid, phosphoric acid, carboxylic acids or sulfonic acids, such as acetic acid, citric acid, benzoic acid, maleic acid, fumaric acid, tartaric acid and p-toluenesulfonic acid.

Preferred compounds of the formula I are those in which a) X is N, Y is $CR^2$ and Z is $CR^2$;

b) X is $CR^2$, Y is N and Z is $CR^2$;

c) X is $CR^2$, Y is $CR^2$ and Z is N or d) X, Y and Z are each N, with c) being particularly preferred.

Further preferred compounds of the formula (I) are those in which a) $R^1$ is
  1. $(C_3-C_{10})$-alkyl,
  2. $(C_3-C_{10})$-alkenyl,
  3. $(C_3-C_{10})$-alkynyl,
  4. $(C_3-C_8)$-cycloalkyl,
  5. benzyl or
  6. benzyl which is substituted as described above;

b) $R^2$ is
  1. hydrogen,
  2. halogen,
  3. nitro,
  4. $C_vF_{2v+1}$,
  5. pentafluorophenyl,
  6. cyano,
  7. phenyl,
  8. phenyl-$(C_1-C_3)$-alkyl,
  9. $(C_1-C_{10})$-alkyl,
  10. $(C_3-C_{10})$-alkenyl,
  11. phenyl-$(C_2-C_6)$-alkenyl,
  12. 1-imidazolyl-$(CH_2)_m-$,
  13. 1,2,3-triazolyl-$(CH_2)_o-$,
  14. tetrazolyl-$(CH_2)_m-$,
  15. $-(CH_2)_{0-1}-CHR^7-OR^5$,
  16. $-(CH_2)_o-O-COR^3$,
  17. $-COR^8$,
  18. $-(CH_2)_o-CO-R^8$,
  19. $-S(O)_rR^6$,
  20. $-CH=CH-(CH_2)_m-CHR^3-OR^6$,
  21. $-CH_2=CH-(CH_2)_m-CO-R^8$,
  22. $-(CH_2)_o-NH-CO-OR^8$,
  23. $-(CH_2)_o-NH-SO_2-R^9$,
  24. $-(CH_2)_nF$,
  25. $-(CH_2)_o-SO_3R^9$,
  26. $-(CH_2)_n-SO_2-NH-CO-NR^6R^9$ or
  27. a radical which is defined as under b) 7., 8., 9., 10. or 15. and is substituted as described above under c) 44., 45. or 46, in each case for a radical of this type;

c) $R^8$ is hydrogen; $(C_1-C_5)$-alkyl, $OR^5$ or $NR^{11}R^{12}$ or morpholino;

d) T is
  1. a single bond,
  2. $-CO-$,
  3. $-CONR^{21}-$,
  4. $-CH_2-CH_2-$,
  5. $-NR^{21}-CO-$,
  6. $-O-CH_2-$, 7. —CH$_2$—O—,
8. —S—CH$_2$—,
9. —CH$_2$—S—,
10. —NH—CH$_2$—,
11. —CH$_2$—NH— or
12. —CH=CH— and the other radicals and variables are as defined above.

Particularly preferred compounds of the formula (I) are those in which a) R$^1$ is (C$_3$-C$_7$)-alkyl, (C$_3$-C$_7$)-alkenyl or (C$_3$-C$_7$)-alkynyl;
b) R$^2$ is
   1. chlorine,
   2. bromine,
   3. C$_v$F$_{2v+1}$ with v=1, 2 or 3,
   4. pentafluorophenyl,
   5. —S(O)$_r$R$^6$,
   6. (CH$_2$)$_{0-1}$—CHR$^7$—OR$^5$,
   7. (CH$_2$)$_0$—O—CO—R$^3$,
   8. —COR$^8$,
   9. —(CH$_2$)$_0$—CO—R$^8$,
   10. —CH$_2$—NH—CO—R$^8$,
   11. —(CH$_2$)$_o$—NH—SO$_2$—R$^9$,
   12. —CH=CH—CHR$^3$—OR$^6$,
   13. tetrazolyl-(CH$_2$)$_m$—,
   14. —(CH$_2$)$_n$SO$_2$—NH—CO—NR$^6$R$^9$,
   15. —(CH$_2$)$_0$—SO$_3$R$^9$ or optionally hydroxyl-substituted (C$_1$-C$_6$)-alkyl, preferably hydroxymethyl;
c) R$^3$ is hydrogen or (C$_1$-C$_4$)-alkyl;
d) R$^6$ is hydrogen, (C$_1$-C$_4$)-alkyl, (C$_1$-C$_4$)-alkanoyl or, preferably, (C$_2$-C$_9$)-heteroaryl;
e) R$^7$ is hydrogen, (C$_1$-C$_4$)-alkyl, (C$_1$-C$_9$)-heteroaryl or (C$_8$-C$_{12}$)-aryl-(C$_1$-C$_4$)-alkyl;
f) R$^8$ is hydrogen, (C$_1$-C$_4$)-alkyl, OR$^5$ or morpholino;
g) R$^9$ is CF$_3$, (C$_1$-C$_6$)-alkyl or phenyl;
h) R$^{14}$ is
   1. (C$_1$-C$_4$)-alkyl,
   2. (C$_1$-C$_4$)-alkoxy,
   3. cyano,
   4. amino,
   5. nitroso,
   6. nitro,
   7. fluorine,
   8. chlorine,
   9. bromine,
   10. hydroxyl,
   11. CH$_2$OR$^7$,
   12. (C$_1$-C$_9$)-heteroaryl-CH$_2$—,
   13. (C$_1$-C$_4$)-alkanoyloxy,
   14. (C$_1$-C$_4$)-alkanoyl,
   15. benzoyl, 16. 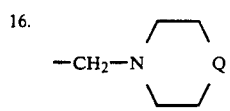

17. —NH—CO—R$^7$ or
   18. tetrazolyl;
R$^{15}$ is
   1. (C$_1$-C$_4$)-alkyl,
   2. (C$_6$-C$_{12}$)-aryl,
   3. (C$_1$-C$_3$)-alkanoyloxy,
   4. (C$_1$-C$_4$)-alkoxy,
   5. (C$_1$-C$_9$)-heteroaryl, preferably 5-tetrazolyl,
   6. cyano,
   7. nitro,
   8. hydroxyl,
   9. —S(O)$_r$R$^6$,
   10. —SO$_3$R$^3$,
   11. chlorine,
   12. bromine,
   13. benzoyl,
   14. —CO$_2$R$^3$ :,
   15. —CO—NH—R$^6$,
   16. —NR$^6$R$^7$,
   17. —CO—R$^8$,
   18. —SO$_2$—NR$^6$R$^7$,

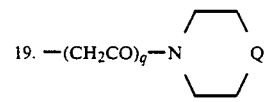

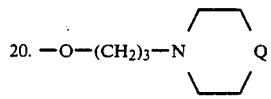

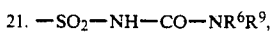

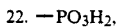

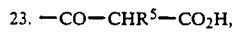

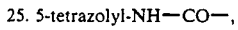

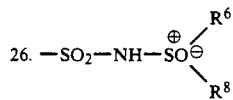

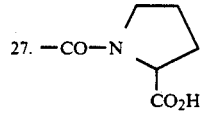

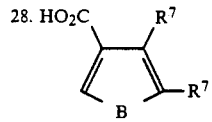

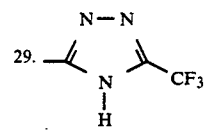

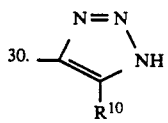

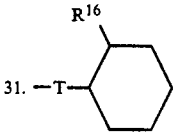

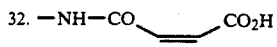

34. the radical defined under i) 2. substituted as defined above;

j) Q is $CH_2$, NH or O;

k) $R^{18}$ is hydrogen, methyl or ethyl;

l) T is a single bond, —O—, —CO—, —NHCO— or —$OCH_2$—, and the other radicals and variables are as defined above.

Very particularly preferred compounds of the formula (I) are those where the symbols $R^2$, $R^9$, $R^{14}$, $R^{15}$, Z, X, Y and q have the following meaning:

$R^2$ chlorine, bromine, —$S(O)R^6$, or —$COR^6$, $R^9$ ($C_1$-$C_6$)-alkyl;

$R^{14}$ tetrazolyl;

$R^{15}$ —$CO_2$—$R^3$, —$SO_2$—$NR^6R^7$, —$SO_2$—NH—CO—$NR^6R^9$ or —NH—CO—NH—$SO_2$—$CH_2$—$R^5$

Z equals N;

X and Y are both $CR^2$;

q zero;

L $CH_2$;

The invention also relates to a process for preparing compounds of the formula I, which comprises alkylating compounds of the formula (II)

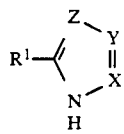
(II)

in which $R^1$, X, Y and Z are as defined above, with compounds of the formula III

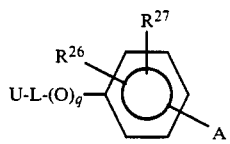
(III)

in which L, A and q are as defined above, and U is a leaving group, where appropriate eliminating again protective groups which have been introduced temporarily, and converting the resulting compounds of the formula (I) where appropriate into their physiologically tolerated salts.

Suitable leaving groups U are preferably nucleofugic groups (cf. Angew. Chem. 72 (1960) 71) such as halogen, o-toluenesulfonate, mesylate or triflate.

Processes for the preparation of the precursors of the formula (II) are disclosed in, inter alia, U.S. Pat. No. 4,355,044, EP-A 324 377 and EP-A 323 841.

Further processes are described in G. L'abbe (Chem. Rev. 69, 345 (1969)); T. Srodsky (in "The Chemistry of the Azido Group", Wiley, New York, 1971, p. 331); H. Wamhoff (in "Comprehensive Heterocyclic Chemistry", A. Katritzky Ed., Pergamon Press, New York (1984)). Another process starts from 1-cyanoglyoxylic acid 2-oxime derivatives and provides after reduction of the oxime with reducing agents known from the literature and addition of mercapto compounds onto the cyano group using suitable protective groups precursors which can be cyclized to imidazoles under water-eliminating conditions. It is possible to use for the cyclization step inter alia mixtures of $PCl_5$ and dimethylaminopyridine (DMAP), $POCl_3$ and $SOCl_2$ and mixtures thereof with DMAP.

The thio compounds are oxidized to the corresponding sulfones and sulfoxides preferably with peracids in suitable solvents such as, for example, dichloromethane.

Suitable for the alkylation of the azoles of the formula (II) are, for example, appropriate benzyl halides, tosylates, mesylates or triflates or appropriate alkyl halides, tosylates, mesylates or triflates.

These compounds are prepared in a manner known per se, for example by halogenation of the corresponding methyl precursors. Preferably employed for this is N-bromosuccinimide, see, for example, J. Org. Chem. 44, 4733 (1979) and Helv. Chim. Acta 62, 2661 (1979).

The alkylation is carried out in an analogous manner by processes which are known in principle.

The azole derivative of the formula (II) is, for example, metalated in the presence of a base. Preferred bases are metal hydrides of the formula MH such as, for example, lithium, sodium or calcium hydride in, for example, DMF or DMSO as solvent or metal alkoxides of the formula MOR where R is methyl, ethyl, t-butyl, and the reaction is carried out in the corresponding alcohol, DMF or DMSO. The azole salts formed in this way are dissolved in an aprotic solvent such as DMF or DMSO and mixed with a suitable amount of alkylating reagent.

A possible alternative to the deprotonation of the azole derivatives is, for example, the reaction with potassium carbonate in DMF or DMSO.

The tetrazoles are prepared from the corresponding nitriles by methods known in principle using azides such as, for example, trialkyltin azides or sodium azide.

The reactions are carried out at temperatures below room temperature up to the boiling point of the reaction mixture, preferably between +20° C. and the boiling point of the reaction mixture, for about 1 to 10 hours.

The compounds of the formula I according to the invention have an antagonistic action on angiotensin II receptors and can therefore be used for treating hypertension dependent on angiotensin II. Other possible uses are for heart failure, cardioprotection, myocardial infarct, cardiac hypertrophy, arteriosclerosis, nephropathy, kidney failure and cerebrovascular disorders such as transient ischemic attacks and stroke.

Renin is a proteolytic enzyme which belongs to the class of aspartyl proteases and which is secreted in response to various stimuli (volume depletion, sodium deficiency, β-receptor stimulation) by the juxtaglomerular cells of the kidney into the circulating blood. There it cleaves the decapeptide angiotensin I off the angiotensinogen which is secreted by the liver. Angiotensin I is converted by angiotensin converting enzyme (ACE) into angiotensin II. Angiotensin II plays an essential part in the regulation of blood pressure because it increases blood pressure directly by vasoconstriction. In addition, it stimulates the secretion of aldosterone from the adrenal and, in this way, via inhibition of sodium excretion, increases the extracellular fluid volume which, in turn, contributes to an increase in blood pressure.

Post-receptor effects are, inter alia, stimulation of phosphoinositol turnover ($Ca^{2+}$ release), activation of protein kinase C and facilitation of cAMP-dependent hormone receptors.

The affinity of the compounds of the formula I for the angiotensin II receptor can be determined by measurement of the $^{125}$-angiotensin II or $^3$H-angiotensin II displacement from receptors on zona glomerulosa membranes of bovine adrenals. For this purpose, the prepared membranes are suspended in buffer at pH 7.4. In order to prevent degradation of the radioligands during the incubation, the peptidase inhibitor aprotinin is added. Additionally used are about 14,000 cpm of a tracer with a specific activity of 74 f TBq/mmol (can be purchased from Amersham Buchler) and an amount of receptor protein which binds 50% of the tracer. The reaction is started by adding 50 μl of membrane suspension to a mixture of 100 μl of buffer+aprotinin; 50 μl of buffer with or without angiotensin II or receptor antagonist and 50 μl of tracer. After an incubation time of 60 minutes at 25° C., bound and free radioligand are separated by a filtration using Whatmann ® GFIC filters on a Skatron ® cell collector.

Non-specific binding is prevented by treating the filters with 0.3% polyethyleneimine pH=10 (Sigma, No. 3143). The degree of displacement of the radioligand from the receptor is determined by measuring the radioactivity in a gamma scintillation counter. The IC$_{50}$ values, which means the concentration of the inhibitor for 50% displacement of the ligand, are determined by the method of Chem. et al. J. Theor. Biol. 59, 253 (1970). For the compounds of the formula (I) they are in the range $1 \times 10^{-4} - 1 \times 10^9$ M.

To determine the antagonistic action of the compounds ©f the formula (I), their effect on the increase in blood pressure induced by angiotensin II in anesthetized Sprague-Dawley rats can be measured. The anesthetic used is sodium thiobarbital (Trapanal ®, Byk Gulden) in the dosage 100 mg/kg i.p. The jugular vein is used for the i.v. administration. The blood pressure is measured in the carotid artery. The animals are initially treated with pentolinium tartrate (10 mg/kg i.m.) so that a lower blood pressure level is reached (ganglion blockade). ANG II (Hypertensin (CIBA)) is administered i.v. in a volume of 0.1 ml/100 g at 10-minute intervals. The dose is 0.5 μg/kg. The compounds of the formula (I) are dissolved in distilled water and administered intravenously or intraduodenally in the doses 0.1, 1, 10 and 100 mg/kg.

The compounds of the formula (I) have activity in particular in the range 0.1-100 mg/kg.

The invention likewise relates to pharmaceutical compositions composed of a compound of the formula (I) and other active substances such as, for example, diuretics or non-steroid antiinflammatory active substances. The compounds of the formula (I) can also be used as diagnostic aids for the renin-angiotensin system.

Pharmaceutical products contain an effective amount of the active substance of the formula (I) and, possibly, other active substances together with an inorganic or organic pharmaceutically utilizable excipient. Administration can be intranasally, intravenously, subcutaneously or orally. The dosage of the active substance depends on the warm-blooded species, the body weight, age and on the mode of administration.

The pharmaceutical products of the present invention are prepared in known dissolving, mixing, granulating or coating processes.

For a form for oral administration, the active compounds are mixed with the additives customary for this purpose, such as excipients, stabilizers or inert diluents and converted by customary methods into suitable dosage forms, such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. Preparation can be carried out both as dry and wet granules. Examples of suitable oily excipients or solvents are vegetable or animal oils such as sunflower oil and fish liver oil.

For subcutaneous or intravenous administration, the active compounds or the physiologically tolerated salts thereof are converted, if required with the substances customary for this purpose, such as solubilizers, emulsifiers or other auxiliaries into solutions, suspensions or emulsions. Examples of suitable solvents are: water, physiological saline or alcohols, for example ethanol, propanediol or glycerol, as well as sugar solutions such as glucose or mannitol solutions or a mixture of the various solvents mentioned.

List of abbreviations:

| | |
|---|---|
| DMF | N,N-dimethylformamide |
| NBS | N-bromosuccinimide |
| AIBN | α,α-azobis-isobutyronitrile |
| EI | electron impact |
| DCI | desorption chemical ionization |
| RT | room temperature |
| EE | ethyl acetate |
| DIP | diisopropyl ether |

EXAMPLE 1

2-[4-[(2-n-Butyl-4chloro-5-formyl-imidazol-1-yl)methyl]-phenyl]imidazo[1,2-a]pyridine-3-carboxylic acid a) Ethyl 2-bromo-3-p-tolyl-3oxopropionate 20.4 g of ethyl 3-p-tolyl-3-oxopropionate (Helv. Chim. Acta 57, 2205 (1974)) are dissolved in 20 ml of CCl$_4$. A solution of 6 ml of bromine in 30 ml of CCl$_4$ is added dropwise at −5° C. After 1 hour at −5° C., the mixture is stirred at 20° C. for 3 h and then at 60° C. for 1 h. the solvent is removed. The title compound is used further as crude product; yield 34 g.

b) Ethyl 2-(4-methylphenyl)imidazo[1,2-a]pyridine-3-carboxylate 5.7 g (20 mmol) of the compound from 1a) and 3.76 g (40 mmol) of 2-aminopyridine in 50 ml of absolute EtOH are boiled under reflux for 4 h and then stirred at RT overnight. Concentration is followed by taking up in 1 N NaHCO$_3$ solution and extraction 3× with CH$_2$Cl$_2$. Drying over Na$_2$SO$_4$ is followed by concentration. The crude product is chromatographed on SiO$_2$ with EtOAc/n-heptane (1:2). Crystallization from n-heptane gives 4.1 g of product of melting point 88° C.; MS (DCI)=281 (M+H)

c) Ethyl 2-(4-bromomethylphenyl)imidazo[1,2-a]pyridine-3-carboxylate 3 g (10.7 mmol) of the compound from 1b) in 20 ml of CCl$_4$ are boiled under reflux with 2.1 g (11.8 mmol) of NBS and 200 mg of benzoyl peroxide for 4 h. Cooling is followed by filtration with suction and extraction of the filtrate 2× with NaHCO$_3$ (1 N). The organic phase is dried over Na$_2$SO$_4$ and concentrated. Chromatography on silica gel with EtOAc/n-heptane (0.8:1.2) as mobile phase yields 1.5 g of the title compound as colorless crystals; melting point 131° C.

MS (DCI): 359+361 (M+H)

d) Ethyl 2-[4-[(2-n-butyl-4-chloro-5-formylimidazole-1-yl)methyl]phenyl]imidazo[1,2-a]pyridine-3-carboxylate (A)

0.72 g (2 mmol) of the compound 1 c), 0.37 g (2 mmol) of 2-n-butyl-4-chloroimidazole-5-aldehyde (from EP-A 324 377) and 0.3 g (2.2 mmol) of potassium carbonate in 10 ml of dry DMF are stirred at RT for 3 h. After taking up in water, extraction with EtOAc is carried out (2×). The combined organic phases are washed 3× with $H_2O$ and once with saturated NaCl solution, dried with $Na_2SO_4$ and concentrated. Chromatography on silica gel provides 0.8 g of the title compound and 0.04 g of the 5-chloro-4-formyl isomer B.

A: $^1$H-NMR (270 MHz, CDCl$_3$): δ=9.78 (s, 1H); 9.39 (d, 1H); 7.74 (d, 2H); 7.70 (d, 1H); 7.43 (dt, 1H); 7.09 (d, 2H); 7.03 (dt, 1H); 5.63 (s, 1H); 4.32 (q, 2H); 2.67 (m, 2H); 1.7 (m, 2H); 1.4 (m, 2H); 1.22 (t, 3H); 0.9 (t, 3H) ppm R$_f$(SiO$_2$; EtOAc/n-heptane (1:2))=0.16

B: $^1$H-NMR (270 MHz, CDCl$_3$) δ=9.93 (s, 1H); 9.39 (d, 1H); 7.78 (d, 2H); 7.72 (m, 1H); 7.46 (dt, 1H); 7.08 (d, 2H); 7.02 (dt, 1H); 5.76 (s, 2H); 4.31 (q, 2H); 2.68 (m, 2H); 1.75 (m, 2H); 1.4 (m, 2H); 1.25 (t, 3H); 0.9 (t, 3H) ppm R$_f$(SiO$_2$; EtOAc/n-heptane (1:1))=0.08 e) 2-[4-[(2-n-butyl-4-chloro-5-formyl-imidazol-1-yl)methyl]phenyl]imidazo[1,2-a]pyridine-3-carboxylic acid 0.28 g (0.6 mmol) of isomer A from Example 1d) in 5 ml of ethanol is stirred with 1.2 ml of 1 N NaOH at RT for 18 h (under nitrogen). Dilution with 10% strength KH$_2$PO$_4$ solution is followed by extraction 3× with EtOAc. Washing with saturated NaCl solution is followed by drying with Na$_2$SO and concentration. The crude product is crystallized from isopropyl ether. 0.16 g of the title compound is obtained as colorless crystals, melting point 120°–123° C.

MS (DCI): 437 (M+H)

EXAMPLE 2

2-[4-[(2-n-Butyl-4-chloro-5hydroxymethyl-imidazol-1-yl)methyl]phenyl]-imidazo[1,2-a]pyridine-3-carboxylic acid a) Ethyl 2-[4-(2-n-butyl-4-chloro-5-hydroxymethylimidazol-1-yl)methyl]phenyl]imidazo[1,2-a]pyridine-3-(-carboxylate 0.28 g of compound A from Example 1d) in 10 ml of ethanol is stirred with 0.25 g of sodium borohydride for 45 min. Dilution with 1 N NaOH is followed by extraction 2× with EtOAc. Washing of the organic phase with saturated NaCl solution is followed by drying with Na$_2$SO and concentration. 0.22 g of the title compound is obtained.

$^1$H-NMR (270 MHz, CDCl$_3$): δ=9.4 (dt, 1H); 7.75 (d, 2H); 7.73 (dt, 1H); 7.46 (dt, 1H); 7.05 (m, 3H); 5.3 (s, 2H); 4.5 (s, 2H); 4.3 (q, 2H); 2.6 (m, 2H); 1.7 (m, 2H); 1.48 (m, 2H); 1.25 (t, 3H); 0.9 (t, 3H) ppm MS (FAB): 467 (M+H)

b) 2-[4-[(2-n-Butyl-4-chloro-5-hydroxymethyl-imidazol-1-yl)methyl]phenyl]imidazo[1,2-a]pyridine-3-carboxylic acid 0.22 g of the compound from Example 2a) in 5 ml of ethanol is reacted with 0.9 ml of 1 N NaOH as in Example 1e). 0.14 g of the title compound is obtained as colorless crystals of melting point 173°–175° C. MS (FAB): 439 (M+H)

EXAMPLE 3

2-[4-[(2-n-Butyl-5-carboxy-4-chloro-imidazol-1-yl)methyl]phenyl]imidazo[1,2,-a]pyridine-3-carboxylic acid a) Ethyl 2-[4-[(2-n-butyl-4-chloro-5-ethoxycarbonyl-imidazol-1-yl)methyl]phenyl]imidazo[1,2-a]pyridine-3-carboxylate 0.28 g (0.6 mmol) of compound A from Example 1d) is dissolved in 5 ml of ethanol. 0.15 g of sodium cyanide is added followed by 53 μl of glacial acetic acid and 1.25 g of manganese dioxide. Stirring at RT for 32 h is followed by filtration with suction, washing with ethanol and concentration of the filtrate. After taking up in H$_2$O, the pH is adjusted to 3–4 with 2% HCl, and extraction with CH$_2$Cl$_2$ is carried out. The organic phase is dried with Na$_2$SO$_4$ and then concentrated. The crude product is reacted without further purification.

b) 2-[4-[(2-n-Butyl-5-carboxy-4-chloro-imidazol-1-yl)methyl]phenyl]imidazo[1,2-a]pyridine-3-carboxylic acid The crude product from 3a) is stirred with 2 ml of 1 N NaOH in 3 ml of ethanol at RT for 48 h. Concentration is followed by taking up in water and adjustment of the pH 3 with 2% HCl. Saturation with NaCl is followed by extraction with CH$_x$Cl$_2$, drying with Na$_2$SO$_4$ and concentration. The crude product is purified on silica gel with CH$_2$Cl$_2$/MeOH (2:1). 40 mg of the title compound are obtained.

MS (FAB): 453 (M+H)

EXAMPLE 4

2-[4-[(2-n-Butyl-4-chloro-5-formyl-imidazol-1-yl)methyl]phenyl]imidazo[1,2-a]pyrimidine-3-carboxylic acid a) Ethyl 2-(4-methylphenyl)imidazo[1,2-a]pyrimidine-3-carboxylate 5.7 g of the compound from 1a) are heated with 10 g of 2-aminopyrimidine at 130° C. for 30 min. Cooling is followed by taking up in CH$_2$Cl$_2$ and washing 6× with H$_2$O. Drying over Na$_2$SO$_4$ is followed by concentration. The crude product is purified on silica gel with EtOAc as mobile phase. 3.45 g of the title compound are obtained as colorless crystals, melting point.

MS (DCI): 282 (M+H)

b) Ethyl 2-(4-bromomethylphenyl)imidazo[1,2-a]pyrimidine-3-carboxylate 3.3 g of the compound from 4a) are boiled under reflux with 2.4 g of NBS and 230 mg of benzoyl peroxide in 35 ml of CCl$_4$ for 4 h. The working up was carried out by the processes indicated in Example 1c).

MS (DCI): 360+362 (M+H)

Ethyl 2-[4-(2-n-butyl-4-chloro-5-formylimidazol-1-yl)methyl]-phenyl]imidazo[1,2-a]pyrimidine-3-carboxylate Prepared by the process indicated in Example 1d) from the compound from Example 4b).
MS (FAB) 466 (M+H)

d) 2-(4-[(2-n-Butyl-4-chloro-5-formyl-imidazol-1-yl)methyl]phenyl]imidazo[1,2-a]pyrimidine-3-carboxylic acid Prepared by the process indicated in Example 1e) from the compound from Example 4c). MS (FAB) 438 (M+H)

The Examples of the formula Ia listed in the following Table were prepared in analogy to the procedures indicated in Examples 1–4.

| Example | $R^1$ | $R^2$ | $R^{26}$ | A |
|---|---|---|---|---|
| 5 | n-C$_4$H$_9$ | CH$_2$OH | H | (thiazoline-carboxylic acid group) |
| 6 | n-C$_3$H$_7$ | CHO | 2-Cl | (N-methyl, SC$_6$H$_5$ substituted group with HOOC) |
| 7 | n-C$_4$H$_9$ | CH$_2$OH | H | (tetrahydrothiazine-carboxylic acid group) |
| 8 | CH$_3$CH$_2$CH=CH | CH$_2$OH | H | (tetrahydropyridine-carboxylic acid group) |
| 9 | n-C$_4$H$_9$ | CHO | H | (N-CH$_3$, C$_6$H$_5$, N substituted group with HOOC) |
| 10 | n-C$_4$H$_9$ | CH$_2$OH | 2-OCH$_3$ | (pyrazole group with N-CH$_3$ and HOOC) |
| 11 | n-C$_5$H$_{11}$ | CHO | H | (NHCH$_3$ substituted group with HOOC) |
| 12 | n-C$_4$H$_9$ | CH$_2$OH | H | (N(CH$_3$)$_2$, S substituted group with HOOC) |

-continued

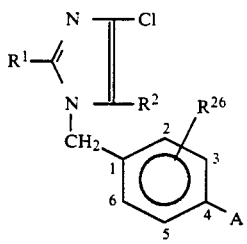

| Example | R¹ | R² | R²⁶ | A |
|---|---|---|---|---|
| 13 | n-C₄H₉ | COOH | H | (structure: HOOC-C=C(CH₃)-O-C(=N-N(CH₃)₂)) |
| 14 | n-C₄H₉ | CH₂OH | H | (structure: tetrahydropyrazine-2-carboxylic acid with methyl) |
| 15 | n-C₄H₉ | CHO | H | (structure: 1,4-dimethyl-1,2,3,4-tetrahydroquinoxaline-2-carboxylic acid) |
| 16 | n-C₃H₇ | CH₂OH | H | (structure: pyrazine with methyl and HOOC) |
| 17 | n-C₄H₉ | CHO | H | (structure: HOOC-C=C(CH₃)-NH-C(=N)-NH₂) |
| 18 | n-C₄H₉ | CH₂OH | 2-OCH₃ | (structure: 5-bromopyridine with methyl and HOOC) |
| 19 | n-C₄H₉ | CHO | H | (structure: bromothiazole with methyl and HOOC) |
| 20 | n-C₃H₇ | CHO | H | (structure: chloropyrazine with methyl and HOOC) |
| 21 | n-C₄H₉ | CH₂OH | H | (structure: 5-chloropyridine with methyl and HOOC) |
| 22 | n-C₃H₇ | CHO | H | (structure: chlorothiazole with methyl and HOOC) |

-continued

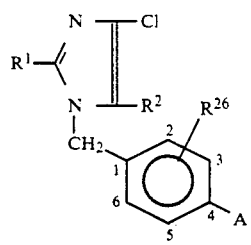

| Example | R¹ | R² | R²⁶ | A |
|---|---|---|---|---|
| 23 | n-C$_4$H$_9$ | CH$_2$OH | H | (4,6-dichloro-pyridazinyl with HOOC, Cl, Cl substituents) |
| 24 | n-C$_4$H$_9$ | CH$_2$OH | H | (hydroxy-pyridazinyl with HOOC, OH) |
| 25 | n-C$_4$H$_9$ | CH$_2$OH | H | (triazinyl with SCH$_3$, NH, HOOC) |
| 26 | n-C$_4$H$_9$ | CH$_2$OH | H | (pyridazinyl with COOH, HOOC) |
| 27 | n-C$_4$H$_9$ | CHO | 2-Cl | (pyridazinyl with CONH$_2$, HOOC) |
| 28 | n-C$_4$H$_9$ | CHOH | H | (pyrimidinyl with NO$_2$, HOOC) |
| 29 | n-C$_4$H$_9$ | CHOH | H | (thiazinyl with S, NO$_2$, HOOC) |
| 30 | n-C$_4$H$_9$ | CH$_2$OH | H | (oxadiazinyl with O, C$_6$H$_5$, HOOC) |
| 31 | n-C$_4$H$_9$ | CH$_2$OH | H | (pyrazolyl with =O, C$_6$H$_5$, HOOC) |
| 32 | n-C$_3$H$_7$ | CHO | H | (thiadiazinyl with S, C$_6$H$_5$, HOOC) |

-continued

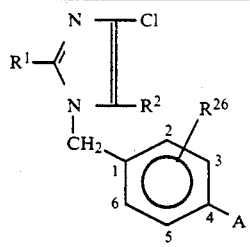

| Example | R¹ | R² | R²⁶ | A |
|---------|-----|------|-------|---|
| 33 | n-C₄H₉ | CHO | H | (structure with N, S, HOOC, C₆H₅) |
| 34 | n-C₄H₉ | CH₂OH | H | (structure with N, COOH, HOOC, NH) |
| 35 | n-C₄H₉ | CHO | 2-OCl₃ | (structure with N, CN, HOOC, NH) |
| 36 | n-C₄H₉ | CH₂OH | H | (structure with N, HOOC, N) |
| 37 | n-C₄H₉ | CHO | H | (structure with N, S, HOOC, COOH) |
| 38 | n-C₄H₉ | CH₂OH | H | (structure with N, N, HOOC, N) |
| 39 | n-C₄H₉ | CHO | H | (structure with N, N, HOOC, NH) |
| 40 | n-C₄H₉ | CH₂OH | H | (structure with N, S, CF₃, HOOC, N) |

EXAMPLE 41

2-[4-[(2-n-Butyl-4-chloro-5-hydroxymethyl-imidazol-1yl)methyl]phenyl]-3-(5-tetrazolyl)imidazo[1,2-a]pyridine a) α-Bromo-2-tolylacetonitrile 15.9 g (0.1 mol) of 3-p-tolyl-3-oxopropionitrile (J. Amer. Chem. Soc. 69, 990 (1974)) are dissolved in 20 ml of CCl₄. A solution of 6 ml of bromine in 30 ml of CCl₄ is added dropwise at −10° C. After 1 h at −8° C., the mixture is stirred at 20° C. for 3 h and then at 60° C. for 1 h. The solvent is removed. The title compound is used further as crude product.

b) 3-Cyano-2-(4-methyl-phenyl)-imidazo[1,2-a]pyridine 4.76 g (20 mmol) of the compound from 41a) and 3.76 g (40 mmol) of 2-aminopyridine are heated without solvent at 120° C. for 30 min. Cooling is followed by chromatography on silica gel with EtOAc/n-heptane (1:3). 3.6 g of product are obtained as an oil.
MS (DCI): 234 (M+H)

c) 2-(4-Bromomethyl-phenyl)-3-cyano-imidazo[1,2-a]pyridine 2.34 g (10 mmol) of the compound from 41b) are dissolved together with 2 g of NBS in 20 ml of chlorobenzene. Addition of 200 mg of benzoyl peroxide is followed by heating at 120° C. for 90 min. Cooling is followed by filtration with suction and washing of the filtrate 2× with 1 N NaHCO₃ solution. The organic phase is dried over Na₂SO₄ and concentrated. Chromatography with SiO₂ (EtOAc/n-heptane 1:2) gives the title compound. MS (DCI): 312+314 (M+H)

d)
2-[4-[(2-n-Butyl-4-chloro-5-formyl-imidazol-1-yl)-methyl]phenyl]-3-cyano-imidazo[1,2-a]pyridine 0.63 g (2 mmol) of the compound from 41c), 0.37 g (2 mmol) of 2-n-butyl-4-chloroimidazole-5-aldehyde and 0.3 g of Na₂CO₃ are reacted in analogy to the procedure indicated in Example 1d). 0.7 g of the title compound is obtained as an oil.
MS (DCI): 418 (M+H)

e)
2-[4-[(2-n-Butyl-4-chloro-5-hydroxymethyl-imidazol-1-yl)-methyl]phenyl]-3-cyano-imidazo[1,2-a]pyridine 0.22 g of the compound from Example 41d) is reacted with 0.2 g of NaBH₄ in analogy to the procedure indicated in Example 2a). 0.2 g of the title compound is obtained.
MS (DCI): 420 (M+H)

f)
2-[4-[(2-n-Butyl-4-chloro-5-hydroxymethyl-imidazol-1-yl)methyl]phenyl]-3-[1(3)-trimethylstannyl-tetrazol-5-yl]-imidazo[1,2-a]pyridine 0.2 g of the compound from Example 41c) is heated with 0.2 g of trimethyltin azide in 5 ml of xylene at 115° C. for 36 h (N₂). Cooling is followed by filtration with suction and washing with toluene. 0.3 g of the title compound is obtained and is further reacted as crude product.

g)
2-[4-[(2-n-Buty-4-chloro-5-hydroxymethyl-imidazol-1-yl)methyl]phenyl]-3-[1(3)-triphenylmethyl-tetrazol-5-yl]imidazo[1,2-a]pyridine 0.3 g of the compound from 41f) in 5 ml of CH₂Cl₂ and 1 ml of tetrahydrofuran is mixed with 10 equivalents of 10 N NaOH. After 5 min, 0.15 g of triphenylchloromethane is added. Stirring at room temperature for 24 h is followed by addition of water, and the organic phase is separated off and concentrated. 0.27 g of the title compound is obtained.
MS (DCI): 703 (M+H)

h)
2-[4-(2-n-Butyl-4-chloro-5-hydroxymethyl-imidazol-1-yl)methyl]phenyl]-3-(tetrazol-5-yl)-imidazo[1,2-a]pyridine 0.27 g of the compound from Example 41f) in 3 ml of methanol is mixed with 1 ml of 5 N HCl. After 2 h at room temperature, the mixture is diluted with methanol and the pH is adjusted to 13 with 10 N NaOH. The methanol is removed in vacuo. The residue is diluted with water and extracted 2× with toluene. The aqueous phase is neutralized with glacial acetic acid, and the product is filtered off with suction. 0.12 g of the title compound is obtained.
MS (DCI): 461 (M+H)

The Examples of the formula Ib which are listed in the following Table were prepared in analogy to the process indicated in Example 41.

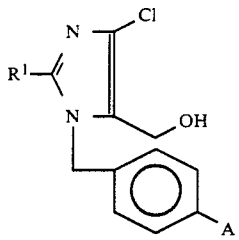

(Ib)

| Example | R¹ | A |
|---|---|---|
| 42 | n-C₄H₉ | |
| 43 | n-C₄H₉ | |
| 44 | n-C₅H₁₁ | |
| 45 | n-C₃H₇ | |
| 46 | n-C₄H₉ | |
| 47 | n-C₄H₉ | |
| 48 | n-C₄H₉ | |

-continued

| Example | R¹ | A |
|---|---|---|
| 49 | n-C₃H₇ | (structure) |
| 50 | n-C₄H₉ | (structure) |
| 51 | n-C₄H₉ | (structure) |

EXAMPLE 52

2-[4-[(3-Methoxymethyl-5-n-propyl-1,2,4-triazol-4-yl)methyl]phenyl]-imidazo[1,2-a]pyridine-4-carboxylic acid a) Ethyl 2-[4-[(3-methoxymethyl-5-n-propyl-1,2,4-triazol-4-yl)methyl]phenyl]-imidazo[1,2-a]pyridine-3-carboxylate Prepared from 2 mmol each of the compound from Example 1c) and 3-methoxymethyl-5-n-propyl-1,2,4-triazole (disclosed in EP-A 323 842) by the process indicated in Example 1d).

MS (DCI): 434 (M+H)

b) 2-[4-[(3-Methoxymethyl-5-n-propyl-1,2,4-triazol-4-yl)methyl]phenyl]-imidazo[1,2-a]pyridine-3-carboxylic acid Prepared from the compound from Example 52a) by the process indicated in Example 1e).

MS (DCI): 406 (M+H)

EXAMPLE 53

2-[4-[(3-Methoxymethyl-5-n-butyl-pyrazol-1-yl)methyl]phenyl]-imidazo[1,2-a]pyridine-3-carboxylic acid a) Ethyl 2-[4-[(3-methoxymethyl-5-n-butyl-pyrazol-1-yl)methyl]phenyl]-imidazo[1,2-a]pyridine-3-carboxylate Prepared from 1.2 mmol of 3-methoxymethyl-5-n-butylpyrazole (as disclosed in EP-A 323 842), 1.5 mmol of the compound from Example 1c) and 2 mmol of sodium hydride in DMF at 40° C. Working up was carried out in analogy to the process indicated in Example 1d). MS (DCI): 447 (M+H)

b) 2-[4-[(3-Methoxymethyl-5-n-butyl-pyrazol-1-yl)methyl]phenyl]imidazo[1,2-a]pyridine-3-carboxylic acid Prepared from the compound from Example 53a) by the processes indicated in Example 1e). MS (DCI): 419 (M+H)

EXAMPLE 54

2-[4-[(2-n-Butyl-4-methylthio-5-carboxy-imidazol-1-yl)methyl]phenyl]-imidazo[1,2-a]pyridine-3-carboxylic acid a) Ethyl 2-amino-2-cyanoacetate 119 g of sodium dithionite are added in portions (15 min) at room temperature to 35 g (0.246 mol) of ethyl 2-cyanoglyoxylate 2-oxime in 350 ml of H₂O and 280 ml of saturated sodium bicarbonate solution.

The mixture is subsequently heated at 35° C. for 1 hour and then saturated with NaCl and extracted 5× with dichloromethane. The organic phase is dried over calcium chloride and then concentrated. 11.8 g of the title compound are obtained as an oil.

$R_f$(CH₂Cl₂/CH₃OH 9/1)=0.6 b) Ethyl 2-cyano-2-n-butylcarbonylaminoacetate 3.39 ml (28.09 mmol) of valeroyl chloride in 5 ml of CH₂Cl₂ are added dropwise at −5° C. to 0° C. to 3.6 g (28.09 mmol) of compound 2a) in 50 ml of dry CH₂Cl₂ and 2.3 ml (28.09 mmol) of pyridine. The mixture is then stirred at room temperature for 1 hour. The organic phase is then washed 3× with H₂O and 1× with saturated NaCl solution, dried over calcium chloride and concentrated.

Crystallization from DIP provides 1.7 g of the title compound.

$R_f$(CH₂Cl/2/CH₃OH 9/1)=0.35

Melting point: 87° C.

c) Ethyl 3-amino-2-n-butylcarbonylaminomethylthioacrylate 2 ml (27.26 mmol) of condensed methyl mercaptan are added at room temperature to 2.9 g (13.67 mmol) of compound 2b) and 0.19 ml (1.36 mmol) of triethylamine in 60 ml of absolute ethanol. After 3 days, a further 0.5 ml of methyl mercaptan is added. After a further 24 hours at room temperature, a further 0.5 ml of methyl mercaptan and 0.19 ml of triethylamine are injected in, and the mixture is stirred at room temperature for a further hours. The solvent is subsequently removed, and the residue is crystallized from DIP, resulting in 2.4 g of the title compound.

$R_f$(CH₂Cl₂/EA 4/1)=0.3

Melting point: 120° C.

d) Ethyl 2-n-butyl-4-methylthioimidazole-5-carboxylate 2.44 g (20.0 mmol) of 4-dimethylaminopyridine in 12 ml of CH₂Cl₂ are added dropwise at −78° C. to 4.17 g (20.0 mmol) of phosphorus pentachloride in 20 ml of CH₂Cl₂. After 5 min, 2.42 g (10.0 mmol) of compound 2c in 25 ml of CH₂Cl₂ are added dropwise. The mixture is then allowed to reach room temperature and is diluted with 30 ml of CH₂Cl₂. After 2 hours, 300 ml of 1 N sodium bicarbonate solution are added while cooling in ice and the mixture is stirred for 1 hour. The phases are then separated, the aqueous phase is extracted 3× with EA, and the combined organic phases are dried with calcium chloride. Chromatography on SiO₂ with CH₂Cl₂/EA (9/1)

$R_f$(CH₂Cl₂/EA 9/1)=0.6 MS (DCI)=243 (M+ +H)

e) Ethyl 2-[4-[(2-n-butyl-4-methylthio-5-ethoxycarbonyl-imidazol-1-yl)-methyl]-phenyl)-imidazo[1,2-a]pyridine-3-carboxylate 0.71 g (1.97 mmol) of the compound from Example 1c), 0.48 g (1.97 mmol) of the compound from Example 54d) and 0.90 g (6.48 mmol) of potassium carbonate are stirred in 10 ml of abs. DMF at room temperature for 24 h. The reaction solution is evaporated to dryness, the residue is dissolved in EA, and the EA solution is washed 3× with $H_2O$ and 1× with saturated $NaHCO_3$ solution, dried over $Na_2SO_4$ and concentrated. Chromatography on silica gel with EA/heptane 1/1 and 4/1 provided 0.51 g of the title compound as an oil.

$R_f$($SiO_2$, EA/heptane 4/1)=0.4
MS (FAB): 521 (M+H)

f) 2-[4-[(2-n-Butyl-4-methylthio-5-carboxy-imidazol-1-yl)-methyl]-phenyl]-imidazo[1,2-a]pyridine-3-carboxylic acid 0.2 g (0.395 mmol) of the compound of Example 54e) was stirred in 5 ml of ethanol with 4 ml of 1 N NaOH at RT for 5 d. The reaction solution was diluted with $H_2O$, adjusted to pH 3 with 2 N $H_2SO_4$ and extracted with EA. The precipitate formed on concentration of the EA solution was filtered off with suction and dried under high vacuum. 60 mg of the title compound resulted. m.p.=199° C. (decomposition) MS (FAB): 493 (M+H)

EXAMPLE 55

2-[4-[(2-n-Butyl-4-methylsulfinyl-5-carboxy-imidazol-1-yl)-methyl]-phenyl]imidazo[1,2-a]pyridine-3-carboxylic acid a) Ethyl 2-[4-[2-n-butyl-4-methylsulfinyl-5-ethoxycarbonyl-imidazo-1-yl)-methyl]-phenyl]-imidazo[1,2a]pyridine-3-carboxylate 300 mg (0.577 mmol) of the compound from Example 54e) were stirred in 10 ml of abs. $CH_2Cl_2$ with 0.199 g (0.577 mmol) of 3-chloroperoxybenzoic acid (50% strength solution) at room temperature for 3 h. 10% strength sodium bisulfite solution was added, the mixture was extracted with EA, and the combined organic phases were washed with 10% strength $Na_2CO_3$ solution, dried over $Na_2SO_4$ and concentrated. Chromatography on silica gel yields 250 mg of the title compound.
MS (FAB): 537 (M+H)

b) 2-[4-[2-n-Butyl-4-methylsulfinyl-5-carboxy-imidazol-1-yl)methyl]-phenyl]-imidazo[1,2-a]pyridine-3-carboxylic acid 250 mg (0.466 mmol) of the compound from Example 55a) were converted into the title compound by the process indicated in Example 54f). 50 mg resulted. MS (FAB): 481 (M+H)

EXAMPLE 56

2-[4-[2n-Butyl-4-methylsulfonyl-5-carboxy-imidazol-1-yl)methyl]-phenyl]-imidazo[1,2-a]pyridine-3-carboxylic acid a) Ethyl 2-[4-[2n-butyl-4-methylsulfonyl-5-carboxyimidazol-1-yl)methyl]-phenyl]-imidazo[1,2-a]pyridine-3-carboxylate 200 mg (0.385 mmol) of the compound from Example 54e) were boiled under reflux in 10 ml of abs. $CH_2Cl_2$ with 0.266 g (0.77 mmol) of 3-chloroperoxybenzoic acid (50% strength) for 15 h. 10% strength sodium bisulfite solution was added to the reaction solution, which was then extracted with EA, and the combined organ. Phases were washed with 10% strength $Na_2CO_3$ solution, dried over $Na_2SO_4$ and concentrated. Chromatography on silica gel with EA/heptane (4:1) provided 130 mg of the title compound.
MS(FAB): 553 (M+H)

b) 2-[4-2-n-Butyl-4-methylsulfonyl-5-carboxy-imidazol-1-yl)methyl]-phenyl]-imidazo[1,2-a]pyridine-3-carboxylic acid The title compound was prepared from the compound from Example 56a) by the process indicated in Example 54f). MS (FAB): 497 (M+H)

EXAMPLE 57

2-[4-[(2-n-Butyl-4-methylthio-5-carboxy-imidazol-1-yl)methyl]-phenyl]-3-(1H-5-tetrazolyl)-imidazo[1,2-a]pyridine a) 2-[4-[(2-n-Butyl-4-methylthio-5-ethoxycarbonylimidazol-1-yl)-methyl]phenyl]-3-cyanoimidazo[1,2-a]-pyridine 1.09 g (3.5 mmol) of the compound from Example 41c), 0.85 g (3.5 mmol) of the compound from Example 54d) and 1.45 g (10.5 mmol) of $K_2CO_3$ are reacted in analogy to the procedure indicated in Example 54e). 1.0 g of the title compound is obtained as a solid with a pale beige color. m.p.=168° C. MS (FAB): 474 (M+H)

b) 2-[4-[(2-n-Butyl-4-methylthio-5-ethoxycarbonyl-imidazol-1-yl)methyl]phenyl]-3-(1H-tetrazol-5-yl)imidazo[1,2-a]pyridine 473 mg (1 mmol) of the compound from Example 57a) are heated to reflux with 310 mg (1.5 mmol) of trimethyltin azide in 3 ml of toluene for 3 h. The reaction solution was diluted with 2 ml of diethyl ether, and 20 ml of saturated KF solution and 0.2 ml of $HBF_4$ solution (50% strength) were added and the mixture was stirred at room temperature for 16 h. The mixture was diluted with EA and filtered, and the EA phase was separated off and dried over $Na_2SO_4$. Concentration of the EA phase and chromatography on silica gel with EA/methanol (3:1) provided 34.0 mg of the title compound.

m.p.: 180°–215° C.
MS (FAB): 517 (M+H)

c)
2-[4-(2-n-Butyl-4-methylthio-5-carboxy-imidazol-1-yl)methyl]-phenyl]-3-(1H-tetrazol-5-yl)-imidazo-[1,2-a]pyridine 180 mg (0.35 mmol) of the compound from Example 57b) were reacted by the process indicated in Example 54f). 55 mg of the title compound resulted after a reaction time of 5 d.
m.p.: 160° C.
MS (FAB): 489 (M+H)

The examples of the formula Ic listed in the following table were prepared in analogy to the processes indicated in Examples 54–57.

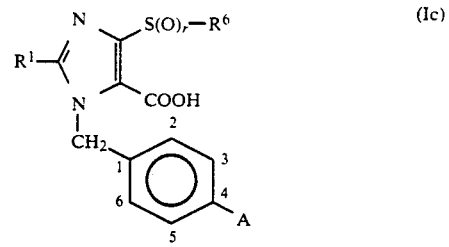

| Example | R$^1$ | r | R$^6$ | A | FAB-MS (M+H) |
|---|---|---|---|---|---|
| 58 | n-C$_3$H$_7$ | 0 | CH$_3$ | imidazo[1,2-a]pyridine-COOH | 451 |
| 59 | n-C$_3$H$_7$ | 2 | CH$_3$ | imidazo[1,2-a]pyridine-COOH | 483 |
| 60 | n-C$_4$H$_9$ | 0 | C$_2$H$_5$ | imidazo[1,2-a]pyridine-COOH | 479 |
| 61 | n-C$_4$H$_9$ | 1 | C$_2$H$_5$ | imidazo[1,2-a]pyridine-COOH | 495 |
| 62 | n-C$_4$H$_9$ | 2 | C$_2$H$_5$ | imidazo[1,2-a]pyridine-COOH | 511 |
| 63 | n-C$_4$H$_9$ | 0 | CH$_3$ | imidazo[1,2-a]pyrimidine-COOH | 466 |
| 64 | n-C$_4$H$_9$ | 0 | CH$_3$ | imidazo[1,2-a]pyrimidine-COOH with tetrazole | 490 |
| 65 | n-C$_4$H$_9$ | 0 | CH$_3$ | imidazo-thiazole-COOH | 471 |
| 66 | n-C$_4$H$_9$ | 0 | CH$_3$ | imidazo-thiazole-COOH with tetrazole | 495 |

-continued

| Example | R¹ | r | R⁶ | A | FAB-MS (M−H) |
|---|---|---|---|---|---|
| 67 | n-C₄H₉ | 0 | CH₃ | 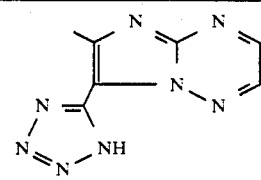 | 491 |
| 68 | n-C₄H₉ | 0 | CH₃ | 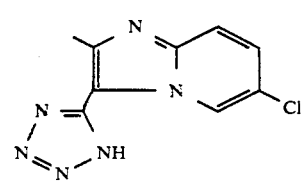 | 523 |

We claim:
1. A compound of the formula I

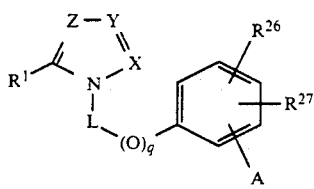

in which
Z is N;
X and Y are CR₂;
R¹ is (C₃-C₇)-alkyl or (C₃-C₇)-alkenyl;
R² is hydrogen, halogen, —CO—OR⁸, —CH₂—OH, —S—(O)₄—(C₁-C₄)-alkyl or —COH;
R³ is hydrogen or (C₁-C₄)-alkyl;
R⁸ is hydrogen or (C₁-C₄)-alkyl;

A is an imidazopyridine or an imidazopyrimidine radical, which radical can be substituted with one radical R¹⁴;
R¹⁴ is cyano, CO₂R³ or tetrazolyl;
L is —CH₂—;
R²⁶ and R²⁷ are hydrogen;
q is zero; and
r is zero or 2,
or a physiologically acceptable salt thereof.

2. A pharmaceutical composition for the treatment of high blood pressure which comprises an effective amount of a composition of the formula I as claimed in claim 1 or a physiologically acceptable salt thereof together with a physiologically acceptable vehicle.

3. A method for the treatment of high blood pressure which comprises administering to a host a pharmaceutical composition as claimed in claim 2.

4. A method for the treatment of high blood pressure which comprises administering to a host an effective amount of a compound of the formula I as claimed in claim 1 or a physiologically acceptable salt thereof.

* * * * *

UNITED STATES PATENT AND TRADEMARK OFFICE
CERTIFICATE OF CORRECTION

PATENT NO. : 5,225,414
DATED : July 06, 1993
INVENTOR(S) : Rainer Henning et al.

It is certified that error appears in the above-indentified patent and that said Letters Patent is hereby corrected as shown below:

Claim 1, column 33, line 38, change " $-S-(O)_4-(C_1-C_4)$-alkyl or $-COH$; " to -- $-S-(O)_r-(C_1-C_4)$-alkyl or $-COH$; --.

Signed and Sealed this

Thirtieth Day of August, 1994

Attest:

BRUCE LEHMAN

Attesting Officer     Commissioner of Patents and Trademarks